(12) United States Patent
Watanabe et al.

(10) Patent No.: US 12,318,416 B2
(45) Date of Patent: Jun. 3, 2025

(54) BIFIDOBACTERIUM GENUS BACTERIUM HAVING HIGH CAPACITY TO UTILIZE POLYSACCHARIDES OF DIETARY ORIGIN

(71) Applicant: KABUSHIKI KAISHA YAKULT HONSHA, Minato-ku (JP)

(72) Inventors: Yohei Watanabe, Minato-ku (JP); Taeko Hara, Minato-ku (JP); Yoshimi Suzuki, Minato-ku (JP); Yuki Saito, Minato-ku (JP); Takahiro Matsuki, Minato-ku (JP)

(73) Assignee: KABUSHIKI KAISHA YAKULT HONSHA, Minato-ku (JP)

(*) Notice: Subject to any disclaimer, the term of this patent is extended or adjusted under 35 U.S.C. 154(b) by 72 days.

(21) Appl. No.: 17/442,459

(22) PCT Filed: Mar. 27, 2020

(86) PCT No.: PCT/JP2020/014045
§ 371 (c)(1),
(2) Date: Sep. 23, 2021

(87) PCT Pub. No.: WO2020/203782
PCT Pub. Date: Oct. 8, 2020

(65) Prior Publication Data
US 2022/0160795 A1    May 26, 2022

(30) Foreign Application Priority Data
Mar. 29, 2019    (JP) .................. 2019-065395

(51) Int. Cl.
| | | |
|---|---|---|
| *A23L 33/135* | (2016.01) | |
| *A61K 35/745* | (2015.01) | |
| *C12N 1/20* | (2006.01) | |
| *A61K 35/00* | (2006.01) | |
| *C12R 1/01* | (2006.01) | |

(52) U.S. Cl.
CPC .......... *A61K 35/745* (2013.01); *A23L 33/135* (2016.08); *C12N 1/205* (2021.05); *A23V 2002/00* (2013.01); *A23V 2400/535* (2023.08); *A61K 2035/115* (2013.01); *C12R 2001/01* (2021.05)

(58) Field of Classification Search
CPC ............ A61K 35/745; A61K 2035/115; A23L 33/135; C12N 1/205; C12N 1/20; C12N 9/2482; A23V 2002/00; A23Y 2035/59; C12R 2001/01; C12Y 302/01008
See application file for complete search history.

(56) References Cited

U.S. PATENT DOCUMENTS

| 5,405,769 A | 4/1995 | Campbell et al. |
| 2007/0274955 A1 | 11/2007 | Gibson et al. |
| 2012/0288585 A1 | 11/2012 | Beier et al. |
| 2018/0037637 A1* | 2/2018 | Benyacoub .......... A61K 35/745 |
| 2021/0139842 A1 | 5/2021 | Odamaki et al. |
| 2021/0244777 A1 | 8/2021 | Odamaki et al. |

FOREIGN PATENT DOCUMENTS

| CN | 1483332 A | 3/2004 |
| CN | 101649303 A | 2/2010 |
| CN | 102703369 A | 10/2012 |
| CN | 102753023 A | 10/2012 |
| CN | 104651337 A | 5/2015 |
| CN | 2016-119877 A | 7/2016 |
| JP | 6-217761 A | 8/1994 |
| JP | 2007-527199 A | 9/2007 |
| WO | WO 2019/112053 A1 | 6/2019 |
| WO | WO 2019/112054 A1 | 6/2019 |

OTHER PUBLICATIONS

Federico Baruzzi, Silvia de Candia, Laura Quintieri, Leonardo Caputo, Francesca De Leo.Development of a Synbiotic Beverage Enriched with Bifidobacteria Strains and Fortified with Whey Protein. 2018 Frontiers in Microbiology pp. 1-8 (Year: 2017).*
Rivière et al., Appl. Environ. Microbiol. 80:204-217, 2014 (Year: 2014).*
Schell et al., PNAS 99:14422-14427, 2002 (Year: 2002).*
Timmerman et al., Int. J. Food Microbiol. 96:219-23, 2004 (Year: 2004).*
UniProt Database Accession No. A0A395ZKB3, Feb. 2019, 2 pages (Year: 2019).*
GenBank Database Accession No. QSWD01000001, Aug. 2018, 1 page (Year: 2018).*
International Search Report issued on Jun. 16, 2020 in PCT/JP2020/014045 filed on Mar. 27, 2020, 3 pages.
Bottacini et al., "Comparative genomics of the *Bifidobacterium breve* taxon", BMC Genomics, 2014, vol. 15, No. 170, pp. 1-18 (19 total pages).
Duranti et al., "Insights from genomes of representatives of the human gut commensal *Bifidobacterium bifidum*", Environmental Microbiology, 2015, vol. 17, No. 7, pp. 2515-2531.
Hori et al., "Utilization by Intestinal Bacteria and Digestibility of Arabinogalactan from Coffee Bean in Vitro", Japanese Journal of Food Microbiology, 2007, vol. 24, No. 4, pp. 163-170 (with English Abstract).
Van Den Broek et al., "Cloning and characterization of arabinoxylan arabinofuranohydrolase-D3 (AXHd3) from *Bifidobacterium adolescentis* DSM20083", Applied Microbiology and Biotechnology, 2005, vol. 67, No. 5, pp. 641-647.
Baruzzi et al., "Development of a Synbiotic Beverage Enriched with Bifidobacteria Strains and Fortified with Whey Proteins", Frontiers in Microbiology, 2017, vol. 8, Article 640, pp. 1-10.

(Continued)

*Primary Examiner* — David Steadman
(74) *Attorney, Agent, or Firm* — Oblon, McClelland, Maier & Neustadt, L.L.P.

(57) ABSTRACT

Provided is a novel *Bifidobacterium* strain capable of utilizing xylans. Bacteria belonging to the genus *Bifidobacterium* having a xylanase gene on a genome.

5 Claims, 2 Drawing Sheets
Specification includes a Sequence Listing.

(56) References Cited

OTHER PUBLICATIONS

"Accession: BAQ29203.1 [GI: 757808417] Definition putative endoxylanase [Bifidobacterium catenulatum subsp.*kashiwanohense* JCM 15439 = DSM 21854]", NCBI Sequence Revision History [online], Oct. 7, 2016, URL:https://www.ncbi.nlm.nih.gov/protein/757808417?sat=3&satkey=37584595, [retrieved on Jun. 9, 2020], which retrieved from the internet:URL:https:///www.ncbi.nlm.nih.gov/protein/BAQ29203.I?report=girevhist, sequence data, 2 pages.
Extended European Search Report issued on May 9, 2023 in European Patent Application No. 20784433.3, 7 pages.
Hidetoshi Morita, et al., "Complete Genome Sequence of Bifidobacterium kashiwanohense JCM 15439T, Isolated from Feces from a Healthy Japanese Infant", Genome Announcements, vol. 3, No. 2, Apr. 30, 2015, XP093042073, doi: 10.1128/genomeA.00255-15, Retrieved on the Intenet: URL:https://www.ncbi.nlm.nih.gov/pmc/articles/PMC4400426/pdf/e00255-15.pdf -& Database Genbank[Online], Oct. 7, 2015, Morita H., et al., "xylanase[Bifidobacterium catenulatum subsp. *kashiwanohense* JCM 15439-Protein-NCBI" XP093042089, Database Accession No. BAQ29205, 3 pages.
Silvia Arboleya, et al., "Gene-trait matching across the Bifidobacterium longum pan-genome reveals considerable diversity in carbohydrate catabolismamong human infant strains", BMC Genomics, vol. 19, No. 1, Jan. 8, 2018, pp. 1-16, XP021252288, DOI: 10.1186/s12864-017-4388-9.
Combined Chinese Office Action and Search Report issued on Jan. 28, 2023 in Chinese Patent Application No. 202080022985.1 (with unedited computer-generated English translation), 30 pages.
An et al., "Integrated Transcriptomic Proteomic Analysis of the Bile Stress Response in a Centenarian-originated Probiotic *Bifidobacterium longum* BBMN68", Molecular & Cellular Proteomics, Oct. 2014, pp. 2558-2572.
Lu, "Advances in Beijing Butter Industrial Technical Researches: 2012-2016", Beijing: Chinese Agricultural University Press, Aug. 2017, p. 243 (with a machine-generated English Abstract) (4 total pages).
Pollet et al., "Functional analysis of glycoside hydrolase family 8 xylanases shows narrow but distinct substrate specificities and biotechnological potential", Appl Microbiol Biotechnol, 2010, vol. 87, pp. 2125-2135.
Combined Chinese Office Action and Search Report issued on Nov. 4, 2023 in Chinese Patent Application No. 202080022985.1 (with unedited computer-generated English translation), 43 pages.

\* cited by examiner

BIFIDOBACTERIUM GENUS BACTERIUM HAVING HIGH CAPACITY TO UTILIZE POLYSACCHARIDES OF DIETARY ORIGIN

TECHNICAL FIELD

The present invention relates to bacteria belonging to the genus *Bifidobacterium* classified as *Bifidobacterium pseudocatenulatum*.

BACKGROUND ART

One of the causes of influence of probiotics on the physiological function of a host is presumed to be that probiotics metabolize carbohydrates sources remaining in the digestive tract and produce short-chain fatty acids such as lactic acid and acetic acid. Previous studies reveal that the genomes of bifidobacterial species dominant in the intestinal tracts of adults have more genes involved in metabolism of plant-derived indigestible polysaccharides, particularly xylans contained in a large amount in diets for adults, in comparison to the genomes of infant-derived bifidobacterial species.

Thus, *Bifidobacterium* strains having a high capacity to utilize indigestible polysaccharides are expected to grow in the intestines of adults and have a high organic acid producing ability, and therefore may become a promising candidate for probiotics for adults.

It has been heretofore known. that as bifidobacteria capable of utilizing indigestible polysaccharides, for example, *Bifidobacterium breve* strains (Non Patent. Literature 1) and *Bifidobacterium bifidum* strains (Non Patent Literature 2) capable of utilizing starch, and *Bifidobacterium pseudocatenulatum* strains (Non Patent Literature 3) capable of utilizing arabinogalactan are present.

However, bifidobacteria. capable of cleaving the xylose backbones of xylans which are typical indigestible polysaccharides contained in the diets have not heretofore been known.

CITATION LIST

Non Patent Literature

Non Patent Literature 1: BMC Genomics (2014) 15:170
Non Patent Literature 2: Environmental Microbiology (2015) 17(7), 25M-2531
Non Patent Literature 3: Japanese Journal of Food Microbiology, Vol.24 No.4 Page. 163-170

SUMMARY OF INVENTION

Technical Problem

The present invention relates to provision of a novel *Bifidobacterium* strain capable of utilizing xylans.

Solution to Problem

The present inventors extensively conducted studies, and resultantly isolated and identified a novel microbial strain capable of efficiently utilizing xylans from the human intestine.

Specifically, the present invention relates to the following 1) to 9).

1) Bacteria belonging to the genus *Bifidobacterium* having a xylanase gene on a genome.

2) The bacteria belonging to the genus *Bifidobacterium* according to 1), wherein the xylanase gene is a polynucleotide consisting of the nucleotide sequence set forth as SEQ ID NO: 1, or a polynucleotide having an identity of 70% or more with the nucleotide sequence and encoding a protein having xylanase activity.

3) The bacteria belonging to the genus *Bifidobacterium* according to 1) or 2), which have an ability to utilize xylans.

4) The bacteria belonging to the genus *Bifidobacterium* according to 3), wherein the xylans are xylan and arabinoxylan.

5) The bacteria belonging to the genus *Bifidobacterium* according to any of 1) to 4), which have an ability to utHlize starch.

6) The bacteria belonging to the genus *Bifidobacterium* according to any of 1) to 5), wherein the bacteria belonging to the genus *Bifidobacterium* are classified as *Bifidobacterium pseudocatenulatum*.

7) *Bifidobacterium pseudocatenulatum* YIT11027 (NITE BP-02928), *Bifidobacterium pseudocatenulatum* YIT11055 (NITE BP-02929), *Bifidobacterium pseudocatenulatum* YIT11057 (NITE BP-02930), *Bifidobacterium pseudocatenulatum* YIT11952 (NITE BP-02931), *Bifidobacterium pseudocatenulatum* YIT11954 (NITE BP-02932), *Bifidobacterium pseudocatenulatum* YIT12989 (NITE BP-02933) or a bacterial strain closely related thereto.

8) A food or beverage comprising the bacteria belonging to the genus *Bifidobacterium* according to any of 1) to 7).

9) The food or beverage according to 8), which is a fermented milk food or beverage.

Advantageous Effects of Invention

The novel bacteria belonging to the genus *Bifidobacterium* according to the present invention have an ability to degrade and utilize xylans contained in a large amount in diets for adults, in particular, arabinoxylan. Thus, the *Bifidobacterium pseudocatenulatum* of the present invention is expected to grow in the intestines of adults and have a high organic acid producing ability, and can be used for medicinal products, food and the like as probiotics for adults.

DESCRIPTION OF EMBODIMENTS

Figure 1:
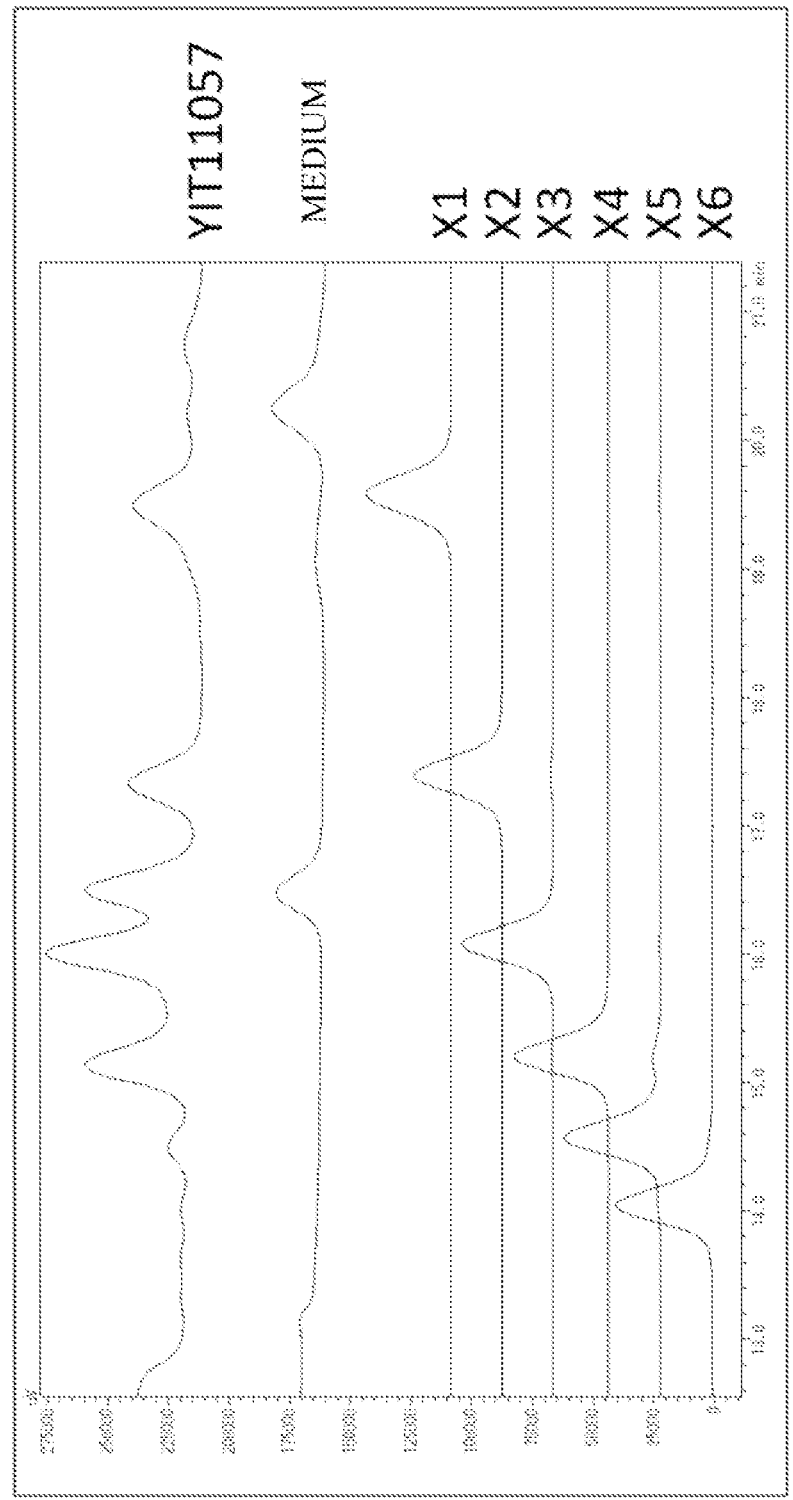
FIG. 1 shows the xylose backbone cleaving activity of the YIT11057 strain.

The type of the bacteria belonging to the genus *Bifidobacterium* of the present invention is not particularly limited as long as the bacteria have a xylanase gene on a genome. The type of the bacteria belonging to the genus *Bifidobacterium* may be any of, for example, *Bifidobacterium pseudocatenulatum*, *Bifidobacterium breve*, *Bifidobacterium longum* (*B. longum*), *Bifidobacterium bifidum* (*B. bifidum*), *Bifidobacterium animalis* (*B. animalis*), *Bifidobacterium suis* (*B. suis*), *Bifidobacterium infantis* (*B. infantis*), *Bifidobacterium adolescentis* (*B. adolescentis*), *Bifidobacterium catenulatum* (*B. catenulatum*), *Bifidobacterium lactis* (*B. lactis*), *Bifidobacterium globosum* (*B. globosum*), *Bifidobacterium angulatum* (*B. angulatum*) and *Bifidobacterium dentium* (*B. dentium*), and is preferably *Bifidobacterium pseudocatenulatum*.

Bifidobacteria having a xylanase gene on the genome have not heretofore been known, and the bacteria belonging to the genus *Bifidobacterium* of the present invention are novel bacteria.

The term "xylanase gene" refers to a gene encoding xylanase classified as GH10 (endo-1,4-beta-xylanase A; xynA), and the "xylanase gene" held by the bacteria belonging to the genus *Bifidobacterium* of the present invention on a genome thereof specifically includes a polynucleotide consisting of the nucleotide sequence set forth as SEQ ID NO: 1 or a polynucleotide having an identity of 70% or more, preferably 90% or more, more preferably 95% or more, still more preferably 98% or more, still more preferably 99% or more with the nucleotide sequence and encoding a protein having xylanase activity.

Here, the polynucleotide consisting of the nucleotide sequence set forth as SEQ ID NO: 1 refers to a xylanase gene held by the later-described YIT11057 strain.

The identity of the nucleotide sequence is a value obtained by aligning two nucleotide sequences to be compared in such a manner that the two nucleic acid sequences are in match with each other as much as possible, dividing the number of matched bases by the total number of bases, and expressing the quotient in percentage. Those skilled in the art can appropriately set parameters of software such as BLAST, ClustalX or Genetyx to determine the identity of the nucleotide sequences.

The term "xylanase activity" means activity of hydrolyzing the xylose backbones of xylans using the xylans as a substrate to produce xylooligosaccharides and xylose (xylan hydrolyzing activity).

Here, examples of the xylans include xylan, arabinoxylan, glucuronoxylan, glucuronoarabinoxylan and acetylxylan, and xylan and arabinoxylan are preferable.

Thus, in other words, the bacteria belonging to the genus *Bifidobacterium* having a xylanase gene on a genome in the present invention are bacteria belonging to the genus *Bifidobacterium* having an ability to cleave the xylose backbones of xylans.

In the present invention, the phrase "having an ability to utilize xylans" means having an ability to grow with xylans as carbon sources. Specifically, the phrase means that, for example, it is possible to grow in a medium containing only xylans as carbon sources. For example, the phrase means that when culturing is performed for 72 hours in a medium containing xylans as the only carbohydrate source, the turbidity is, for example, 0.1 or more in terms of increase in $OD_{600}$. The turbidity is preferably 0.3 or more, more preferably 0.4 or more in terms of increase in $OD_{600}$. When the change of turbidity cannot be measured due to the medium. containing xylans having a large amount of insoluble fractions or for other reasons, the phrase means that the amount of short-chain fatty acids produced in the culture supernatant after 72-hour culturing, for example, the total amount of lactic acid, acetic acid and formic acid produced, is 10 mM or more. The amount of short-chain fatty acids produced is preferably 20 mM or more, more preferably 40 mM or more in total.

The medium to be used in a test on the xylans utilizing ability may he one obtained by adding xylans to a medium free of carbohydrate sources, and the composition of the medium free of carbohydrate sources can. be the composition of M-ILS liquid medium, Peptone-Yeast (PY) medium or the like.

The amount of xylans added to the medium is preferably 0.01 to 10 mass %, more preferably 0.05 to mass %, still more preferably 0.1 to 1 mass % in the medium. It is desirable that as a control, bacteria belonging to the genus *Bifidobacterium* of interest be cultured in a medium free of carbohydrate sources, followed by checking OD values.

As described above, the bacteria belonging to the genus *Bifidobacterium* having a xylanase gene on a genome in the present invention have an ability to degrade and utilize xylans, and therefore can contribute to supply of short-chain fatty acids such as acetic acid, lactic acid and formic acid produced by degradation of xylans.

The bacteria belonging to the genus *Bifidobacterium* of the present invention can be obtained by screening from bacteria belonging to the genus *Bifidobacterium* present in, for example, the intestines of humans (e.g. adults or infants), preferably *Bifidobacterium pseudocatenulatum*, using the presence of a xylanase gene or the above ability to utilize xylans as an indicator. For example, from *Bifidobacterium pseudocatenulatum,* 16 strains shown in. Examples below, and further six strains of YIT11027, YIT11055, YIT11057, YIT11952, YIT11954 and YIT12969 can be selected. The bacteria belonging to the genus *Bifidobacterium* of the present invention are not limited thereto and include bacterial strains which are biologically and genetically closely related thereto, as long as the bacteria belonging to the genus *Bifidobacterium* have a xylanase gene on a genome. The bacteria belonging to the genus *Bifidobacterium* of the present invention may be a natural strain present in nature, a variant of a natural strain, or a genetically modified species as long as they have a xylanase gene on a genome.

As shown below, YIT11027 strain, YIT11055 strain, YIT11057 strain, YIT11952 strain, YIT11954 strain and YIT12989 strain were deposited at the National Institute of Technology and Evaluation, Patent Microorganisms Depositary (#122, Kazusakamatari 2-5-8, Kisarazu-shi, Chiba) on Mar. 25, 2019.

*Bifidobacterium pseudocatenulatum* YIT11027 (NITE BP-02928),
*Bifidobacterium pseudocatenulatum* YIT11055 (NITE BP-02929),
*Bifidobacterium pseudocatenulatum* YIT11057 (NITE BP-02930),
*Bifidobacterium pseudocatenulatum* YIT11952 (NITE BP-02931),
*Bifidobacterium pseudocatenulatum* YIT11954 (NITE BP-02932), and
*Bifidobacterium pseudocatenulatum* YIT12989 (NITE BP-02933).

Of these, the YIT11027 strain, YIT11057 strain, YIT11954 strain or bacterial strains closely related thereto are preferable from the viewpoint of an ability to utilize xylans and further from the viewpoint that they also have a starch-utilization ability in combination. Further, YIT11057 strain or bacterial strains closely related thereto are more preferable from the viewpoint that they have acid/bile acid resistance and also have the properties that no lysogenic phage is detected in the genome.

Here, the term "starch-utilization ability" means having an ability to grow with starch as carbon sources. The term "acid/bile acid resistance" means the viability after continuous exposure to artificial gastric acid and artificial bile acid. The term "no lysogenic phage" means that a region having high homology with an existing phage has not been detected in a genome sequence by use of PHASTER which is a phage search program server.

The term "closely related bacterial strains" indicates bacterial strains having identical sequences in Multilocus sequence analysis (MLSA) for evaluating a plurality of housekeeping gene sequences.

Specifically, the full-length sequences of DNA gyrase subunit B (gyrB), 50S ribosomal protein L2 (rplB), Amidophosphoribosyltransferase (purF), DNA-directed RNA polymerase subunit beta (rpoB), ATP-dependent Clp protease ATP-binding subunit ClpCl (clpC), Elongation factor G (fusA) and Isoleucine-tRNA ligase (ileS) reported as genes suitable for MLSA analysis of bifidobacteria (International Journal of Systematic and Evolutionary Microbiology (2006), 56, 2783-2792) are acquired, all genes are linked for each bacterial strain, and the coincidence in sequence between strains for comparison is then examined using a program such as VSEARCH or BLAST. When the sequence identity is 90% or more, preferably 95% or more, more preferably 98% or more, still more preferably 99% or more, it can be determined that the bacterial strains are closely related species.

The nucleotide sequences of gyrB, rplB, purF, rpoB, clpC, fusA and ileS genes in YIT11057 strain are shown. in the sequence listing (gyrB: SEQ ID NO: 2, rplB: SEQ ID NO: 3, purF: SEQ ID NO: 4, rpoB: SEQ ID NO: 5, clpC: SEQ ID NO: 6, fusA: SEQ ID NO: 7, and ileS: SEQ ID NO: 8).

The application form. of the bacteria belonging to the genus *Bifidobacterium* of the present invention is not particularly limited, and may be lyophilized bacteria, or a cultured product containing these bacteria can be utilized. In any of the forms, the bacteria are preferably in a viable state.

The bacteria belonging to the genus *Bifidobacterium* of the present invention can also be mixed with a solid or liquid pharmaceutical nontoxic carrier and utilized in the form of a common pharmaceutical preparation. Examples of the preparation include solid preparations such as tablets, granules, powders and capsules, liquid. preparations such as solutions, suspensions and emulsions, and lyophilized preparations. These preparations can be prepared by conventional means for production of preparations. Examples of the pharmaceutical nontoxic carrier include glucose, lactose, sucrose, starch, mannitol, dextrin, fatty acid glycerides, polyethylene glycol, hydroxyethyl starch, ethylene glycol, polyoxyethylene sorbitan fatty acid esters, amino acids, gelatin, albumin, water and physiological saline. If necessary, common additives such as stabilisers, wetting agents, emulsifiers, binders, tonicity agents and excipients can also be appropriately added.

The bacteria belonging to the genus *Bifidobacterium* of the present invention can be not only prepared into the above-described preparations but also added to a food or beverage for use. When added. to a food or beverage, the bacteria belonging to the genus *Bifidobacterium* may be incorporated directly or together with various nutrient ingredients. Specifically, when added to a food or beverage, the bacterial belonging to the genus *Bifidobacterium* of the present invention may be made into a form suitable for eating, i.e. a granular form, a particulate form, a tablet, a capsule, a paste or the like using common means with appropriate use of additives usable for food or beverage, may be added to various foods, e.g. processed meat products such as ham and sausage, processed seafood products such as cooked minced fish (kamabcko) and fish sausage (chikuwa), bread, confectionary, butter and dry milk, or may be added to beverages such as water, fruit juice, milk, soft drinks and tea drinks. The food or beverage includes animal feeds.

Further, as the food or beverage, fermented milk food. or beverage and fermented food or beverage such as fermented soybean milk, fermented fruit juice and fermented vegetable juice which contain the bacteria belonging to the genus *Bifidobacterium* of the present invention in a viable state are suitably used, and in particular, the fermented milk food or beverage is preferably used. The fermented milk food or beverage may be produced in accordance with a conventional method, and for example, when fermented milk is produced, the bacteria belonging to the genus *Bifidobacterium* of the present invention is inoculated and cultured in a sterilized milk medium alone or together with other microorganisms, and the cultured product is subjected to homogenization treatment to obtain a fermented milk base. Next, a separately prepared syrup solution is added and mixed, the mixture is homogenized with a homogenizer or the like, and a flavor is further added to make a final product. The fermented milk food or beverage thus obtained can also be a product in any form such as a plain type free of syrup (sweetener), a soft type, a fruit flavor type, a solid form or a liquid form.

To such fermented milk food or beverage, optional ingredients including sweeteners such as syrup, emulsifiers, thickeners (stabilizers) and various vitamins can be added. The following may be added: as the syrup, saccharides such as glucose, sucrose, fructose, high-fructose corn syrup, glucose syrup, palatinose, trehalose, lactose, xylose, galactooligosaccharide (GOS), xylooligosaccharide (XOS), arabinoxylooligosaccharide (AXOS), xylan, arabinoxylan, arabinooligosaccharide (AOS), arabinan, maltose, honey and molasses; sugar alcohols such as sorbitol, xylitol, erythritol, lactitol, palatinit, reduced sugar syrup and reduced maltose syrup; and high intensity sweeteners such as aspartame, thaumatin, sucralose, acesulfame K and stevia; emulsifiers such as glycerin fatty acid esters, polyglycerin fatty acid esters, sorbitan fatty acid esters and lecithin; and thickeners (stabilizers) such as agar, gelatin, carrageenan, guar gum, xanthane gum, pectin, locust bean gum, gellan gum, carboxymethyl cellulose, soybean polysaccharide and propylene glycol alginate. In addition, the following may be added: vitamins such as vitamin A, vitamin B, vitamin C and vitamin E; minerals such as calcium, magnesium, zinc, iron and manganese; acidifiers such as citric acid, lactic acid, acetic acid, malic acid, tartaric acid and gluconic acid; milkfats such as cream, butter and sour cream; flavors based on yogurt, berry, orange, Chinese quince, perilla, citrus, apple, mint, grape, apricot, pear, custard cream, peach, melon, banana, tropical, herb, black tea, coffee and the like; herb extracts, brown sugar extracts and the like.

For production of the fermented milk food or beverage, microorganisms other than the bacteria belonging to the genus *Bifidobacterium* of the present invention can also be used in combination. Examples of such microorganisms include bacteria belonging to the genus *Lactobacillus* such as *Lactcbacillus casei*, *Lactobacillus acidophilus* (*L. acidophilus*), *Lactobacillus plantarum* (*L. plantarum*), *Lactobacillus buchneri* (*L. buchneri*), *Lactobacillus gallinarum* (*L. gallinarum*), *Lactobacillus amylovorus* (*L. amylovorus*), *Lactobacillus brevis* (*L. brevis*), *Lactobacillus rhamnosus* (*L. rhamnosus*), *Lactobacillus kefir* (*L. kefir*), *Lactobacillus paracasei* (*L. paracasei*), *Lactobacillus crispatus* (*L. crispatus*), *Lactobacillus zeae* (*L. zeae*), *Lactobacillus helveticus* (*L. helveticus*), *Lactobacillus salivalius* (*L. salivalius*), *Lactobacillus gasseri* (*L. gasseri*), *Lactobacillus fermentum* (*L. fermentum*), *Lactobacillus reuteri* (*L. reuteri*), *Lactobacillus delbrueckii* subspecies. *bulgaricus* (*L. delbrueckii* subsp. *bulgaricus*), *Lactobacillus delbrueckii* subspecies. *delbrueckii* (*L. delbrueckii* subsp. *delbrueckii*) and *Lactobacillus johnsonii* (*L. johnscnii*), bacteria belonging to the genus *Streptococcus* such as *Streptococcus thermophilus*, bacteria belonging to the genus *Lactococcus* such as *Lactococcus lactis* subspecies. *lactis* (*Lactccoccus lactis* subsp. *lactis*), Lactococcus lactis subspecies. cremoris (Lactccoccus lactis subsp. cremoris), bacteria belonging to the genus Enterococcus such as Enterococcus faecalis and Enterococcus faecium (E. faecium), bacteria belonging to the genus Bacillus such as Bacillus subtilis, and yeasts belonging to Saccharomyses genus, Torulaspora genus and Candida genus such as Saccharomyses cerevisiae, Torulaspora delbrueckii and Candida kefyr. It is preferable that one or more selected from the group consisting of bacteria belonging to the genus Lactobacillus, Streptococcus and Lactococcus be used in combination with the bacteria belonging to the genus Bifidobacterium of the present invention to produce fermented milk food or beverage because a highly pleasant taste can be obtained, so that eating or drinking is facilitated.

When the bacteria belonging to the genus Bifidobacterium of the present invention is used, the dose thereof is not strictly limited, and the suitable dose thereof is preferably $10^5$ cfu to $10^{13}$ cfu, particularly preferably $10^8$ cfu to $10^{12}$ cfu a day in terms of the number of viable bacteria.

EXAMPLES

Example 1: Screening of Bacteria Belonging to the Genus Bifidobacterium having an Ability to Utilize Xylans i) Bacterial Strains Used 53 Strains isolated from human feces and identified as Bifidobacterium pseudocatenulatum were screening targets.

ii) Substrate

Xylan (derived from oat), arabinoxylan (derived from wheat) and xylooligo-saccharide (XOS) industrially produced by enzymatically treating xylan were used for analysis. For xylan and arabinoxylan, the results of examination by HPLC did not show the presence of monosaccharide (data is not shown). In addition, xylose and arabinose which are constituent monosaccharides of xylan and arabinoxylan, respectively, were analyzed, and as controls for confirmation of growth, starch which is a typical indigestible polysaccharide and glucose which is a constituent monosaccharide of starch, and lactose were also analyzed. After a 1% suspension of each substrate was prepared, xylan, arabinoxylan and starch were subjected to autoclave sterilization, and other substrates were subjected to sterilization by filtration using a 0.22 μm filter.

iii) Test on Utilization Properties

For preventing suppression of growth of bacteria due to a growth-associated decrease in pH, an m-PY medium containing 100 mM PIPES was used. The 1% substrate solution was mixed with an equal amount of two-fold concentrated m-PY medium stored under refrigeration in a nitrogen-filled atmosphere until use, and the mixture was used for a culture test (final concentration: 0.5%).

The frozen. bacterial liquid was inoculated in a modified CAM agar, and then cultured for 2 to 3 days, and the thus-obtained colonies were subcultured in a modified GAM liquid medium containing 1% glucose/lactose. In the subculture, care was taken so as to scrape a large number of colonies. Stationary culturing was performed overnight at 37° C., and next morning, the bacterial liquid. in. an amount of 5% was subcultured again in a fresh one of the same medium. The bacterial liquid was cultured for about 6 to 9 hours until reaching the logarithmic growth phase, and the turbidity was then measured. 100 μl of the culture solution. was centrifuged, the supernatant was removed, and a carbohydrate source-free m-PY medium was then added to provide an $OD_{600}$ of 0.2 to suspend pellets. 198 μl of each medium was dispensed to a 96-well plate, 2 μl of the bacterial liquid was added, then 50 μl of mineral oil was overlaid, and the bacteria were cultured at 37° C. in a microplate reader PowerWave 340 (BIOTEC Co., Ltd.).

The turbidity was measured every 30 minutes, and the turbidity was monitored for 60 hours after the start of culturing. The above-described culturing operations were all carried out in an anaerobic glove box. After 60 hours, a portion of the culture solution was taken, deproteinized, and then subjected to IPLC to measure the amount of short-chain fatty acids produced. When a large amount of insoluble particles were present in an m-PY medium containing xylan, the utilization properties were determined based on existence or non-existence of production of short-chain fatty acids because it was impossible to confirm growth of bacterial cells only by the measurement of turbidity. The short-chain fatty acids in the culture supernatant after culturing for 60 hours were measured by HPLC to confirm that the total amount of lactic acid, acetic acid and formic acid produced was 10 mM or more. Table 1 shows the number of strains which were capable of utilizing each of various substrates.

TABLE 1

| | Xylan | Arabinoxylan | XOS | Xylose | Arabinose | Starch | Glucose | Lactose |
|---|---|---|---|---|---|---|---|---|
| Number of utilizing strains | 16 | 16 | 53 | 39 | 36 | 28 | 51 | 53 |
| Number of non-utilizing strains | 37 | 37 | 0 | 14 | 17 | 25 | 2 | 0 |

A capacity to utilize xylooligosaccharides was shown in all bacterial strains of B. pseudocatenulatum, however, a capacity to utilize xylans having a longer chain varied among bacterial strains. 16 Strains which had utilized xylan and arabinoxylan were screened as bacteria belonging to the genus Bifidobacterium having an ability to utilize xylans.

The bacterial strains belonging to the genus Bifidobacterium having an ability to utilize xylans were cultured in a liquid medium with xylan as the only carbohydrate source, and the oligosaccharides in the culture supernatant in the earlier logarithmic growth phase were analyzed by HPLC. The result showed that xylose and xylooigosaccharides had been produced. This revealed that the present bacteria had activity of cleaving the xylose backbone into xylose and xylooligosaccharides. FIG. 1 shows, as a typical example, the results of analysis using YIT11057 strain which is one the 16 strains. Symbols X1 to X6 in FIG. 1 denote xylose and xylooligosaccharides having corresponding numbers of xylose backbones, and it can be seen that xylose and xylooligosaccharides which had not been present in the medium were produced by culturing YIT11057 strain.

Example 2: Properties of Six Strains of YIT11027, YIT11055, YIT11057, YIT11952, YIT11954 and YIT12989

The utilization properties of the six strains of YIT11027, YIT11055, YIT11057, YIT11952, YIT11954 and YIT12989 selected from the above 16 strains having an ability to utilize xylans are shown below. For the three bacterial strains of YIT11027, YIT11057 and YIT11954, it was possible to confirm the starch-utilization properties as well as the xylan-utilization properties (Table 2).

TABLE 2

|  | Xylan | Arabinoxylan | XOS | Xylose | Arabinose | Starch | Glucose | Lactose |
|---|---|---|---|---|---|---|---|---|
| YIT 11027 | + | + | + | + | + | + | + | + |
| YIT 11055 | + | + | + | + | + | − | + | + |
| YIT 11057 | + | + | + | − | − | + | + | + |
| YIT 11952 | + | + | + | + | + | + | + | + |
| YIT 11954 | + | + | + | + | + | + | + | + |
| YIT 12989 | + | + | + | + | + | − | + | + |
| YIT 4037T (type strain) | − | − | + | + | + | + | + | + |

+: utilization properties found
−: non-utilization properties

Example 3: Genomic Analysis

Genomic DNA was extracted from the bacterial cells, and a draft genome was determined using a next-generation sequencer Miseq (Illumina, Inc.). The gene region was predicted, and then the carbohydrate-active enzyme gene database dbCAN was consulted for all amino acid sequences to extract carbohydrate-active enzyme genes. The result of searching for genes identical in capacity to utilize xylans and distribution showed that all of the strains having endo-1,4-beta-xylanase A gene (xynA) belonging to GH10 were capable of utilizing xylans. Any of the strains which do not have this gene was not capable of utilizing xylans.

Example 4: Properties of YIT11057

For YIT11057, acid/bile acid resistance, exhaustive searching for pathogenic factors and detection of a lysogenic phage in the genome were evaluated.
1) Acid/Bile Acid Resistance
   i) Artificial juice composition
   <Artificial gastric juice composition (pH 3.6)>
   Pepsin 40 mg/L
   Proteose peptone 5 g/L
   Gastric mucin 1.5 g/L
   NaCl 5 g/L
   NaHCO$_3$ 3 g/L
   KH$_2$PO$_4$ 1 g/L
   3.6 N HCl adjusting pH to 3.6

Figure 2:
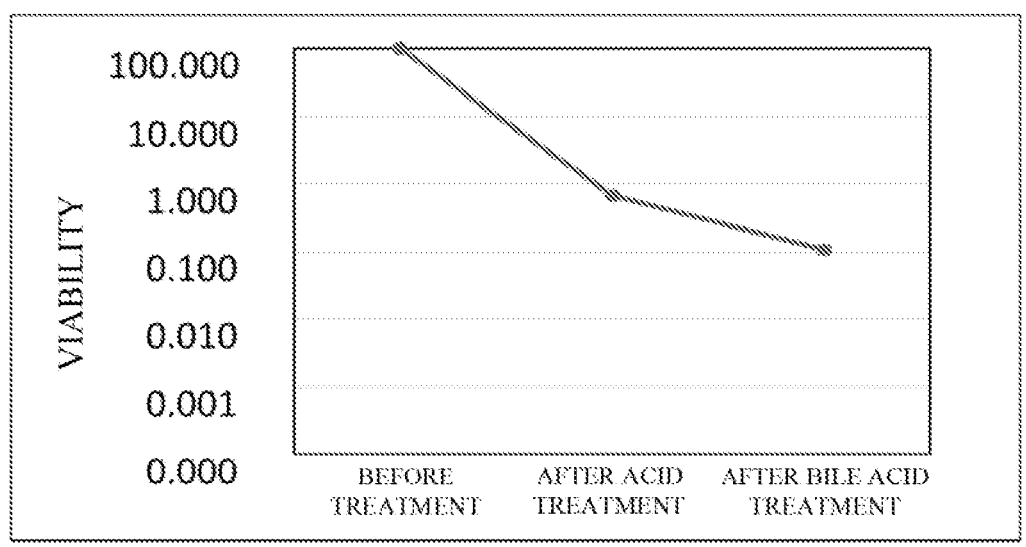
FIG. 2 shows the acid/bile acid resistance of the YIT11057 strain.

<Artificial intestinal juice>
   NaCl 5 g/L
   KCl 1 g/L
   NaHCO$_3$ g/L
   3 M Na$_2$CO$_3$ adjusting pH to 8.0
   ii) 0.1 ml of a bacterial liquid cultured overnight in an mGAM liquid medium containing 1% glucose/lactose was added to 2 ml of artificial gastric juice, and the mixture was incubated at 37° C. for 1 hour. Thereafter, 5.5 ml of artificial intestinal juice and 0.5 ml of 16% bile acid were added, and the mixture was left to stand at 37° C. for 1 hour. Before and after acid treatment and after bile acid treatment, the bacterial liquid was collected, and diluted with physiological saline, 50 of the diluted liquid was then applied to an mGAM agar, and CFU was measured. The result showed that the viabilty rate was about 0.1% even after bile acid treatment (FIG. 2). Since CFU of bacteria without resistance after each of the treatments was equal to or less than the detection lower limit, YIT11057 was shown. to have relatively high acid/bile acid resistance.
2) Exhaustive Searching for Pathogenic Factors
   Draft genome information was input in the PATRIC server (Wattam et al., 2017), and existence or non-existence of genes having high homology with sequences in the Virulence Factor database was examined. As a result, a pathogenic factor gene was not detected.
3) Detection of Lysogenic Phages in Genome
   For genome information of bacterial strains, an attempt was made to detect lysogenic phages registered in the phage database using the PHASTER server (Arndt et al., 2016). As a result, a lysogenic phage was not detected.

---

The invention claimed is:

1. A method of improving digestion of indigestible polysaccharides comprising xylans in a subject, the method comprising:
   providing an ingestible composition to a subject to thereby improve digestion of indigestible polysaccharides comprising xylans,
   wherein the ingestible composition metabolizes indigestible polysaccharides comprising xylans,
   wherein the ingestible composition comprises viable *Bifidobacterium pseudocatenulatum* bacteria having a genomic xylanase gene, and
   wherein the nucleotide sequence of the genomic xylanase gene comprises the nucleotide sequence of SEQ ID NO: 1.

2. The method according to claim 1, wherein the xylans are xylan and arabinoxylan.

3. The method according to claim 1, wherein the *Bifidobacterium pseudocatenulatum* bacteria have an ability to utilize starch.

4. A method for improving digestion of indigestible polysaccharides comprising xylans in a subject, the method comprising:
   providing an ingestible composition to a subject to thereby improve digestion of indigestible polysaccharides comprising xylans,
   wherein the ingestible composition comprises a viable *Bifidobacterium pseudocatenulatum* bacterium, and
   wherein the viable *Bifidobacterium pseudocatenulatum* bacterium is *Bifidobacterium pseudocatenulatum* YIT11027 having National Institute of Technology and Evaluation (NITE) deposit number NITE BP-02928, *Bifidobacterium pseudocatenulatum* YIT11055 having NITE deposit number NITE BP-02929, *Bifidobacterium pseudocatenulatum* YIT11057 having NITE deposit number NITE BP-02930, *Bifidobacterium pseudocatenulatum* YIT11952 having NITE deposit number NITE BP-02931, *Bifidobacterium pseudocatenulatum* YIT11954 having NITE deposit number NITE BP-02932, or *Bifidobacterium pseudocatenulatum* YIT12989 having NITE deposit number NITE BP-02933.

5. The method according to claim 1, wherein the indigestible polysaccharides are contained in a food or beverage composition.

\* \* \* \* \*

SEQUENCE LISTING

<160> NUMBER OF SEQ ID NOS: 8

<210> SEQ ID NO 1
<211> LENGTH: 2592
<212> TYPE: DNA
<213> ORGANISM: Bifidobacterium pseudocatenulatum

<400> SEQUENCE: 1

-continued

```
gtgaaggagg tgcgagcgaa cgggttcggg ggcagagtag ctgccgaacc gaacggcccg    60
atacgcgggc tacgcaagga atacaccatt atcaatgagg aaagtgatgg atacacattg   120
ttcaatacaa ccgatgaacg tggggcgtcc aagcgccgtg gcatcgtcgc ggcgcttgcg   180
gccgtagcca tgctggtgcc gctggcattc gctccgtcgg ctaccgccgc ggaaggcgac   240
tactccggtg gcatcaaggg cgagtacaac gctctgggca tcgccgccgg tgtggcgacc   300
gaagcctata gcggtctcaa tagccaggaa cggcaggata cggtgcttgc caacttcaac   360
cagatcactc cggaaaactc gatgaagccg gaaggctggt acgacggcaa tcatgagttc   420
gccatgtccg ataacacccg gagcctgttg aagttcgcca gcgacaacaa catccggatc   480
tacggccacg ttctggtgtg gcactccag acgcccgact ggttcttcca agcggacgaa    540
tggtgtgagg acgccaataa caccgccggt gtcaccagct gccgctggc cgacaaggcc    600 acgatgcagg agcgtcagcg tcagcacatc gagaacgtcg ccaaggcgat ctccgatgag   660
ttcggtccgt tcggcagcga cacgaatccc gtcgtggcgt tcgatgtcgt caacgaaacc   720
gtgaacgaca ccgacaatcc ggacaccaac ggcatgcgca attcgctgtg gtaccagacc   780
tacgacggtg aggactacat ctatgacgcg ttcgagaatg cgaacacgta cttcaacgag   840
gtgtacgccg atccttcgga cgatcatccg gtgacgttgt tcatcaacga ttacaacacc   900
gagcagtcgg gtaagcgcac ccggtatgct gccctgctgg accgtatggt tgccgaaggc   960
gtgccgttcg acggcatcgg ccaccagttc catgtgacgt tgaccacggc gacctcgaac  1020
ctggaggccg cgctgaccga catggaacgc ttcaacaaga agcaggccat caccgaactg  1080
gacgtgacga ccggaacccc ggtcacggag gccaagctca tcgaacaggg ccagtactac  1140
tatgaagtaa atcagatcat ccaccgtcac gctgcgcagc tgttctccgt tacggtgtgg  1200
ggcttgatcg acggactgtc ctggcgtagt ggcgaaggcg ctccgctgct gttcgacgac  1260
aacctggaga agaagccggc gtacatcggc tacatcggtg atagcgccaa ccttcccgag  1320
ccgttgaaga gcatgaacgc attcaaggat gacgccgtgg gcatcgactc ggcgcttccc  1380
ggtaccgtgg ccgagtccgg cgcgtcctct ccgtgggaac gtctttcgct ggtcgagatg  1440
accccgtctg cgaatggcgc cgtttccggc tcgttcaatg tctattggaa ggacggctct  1500
ctggtcgtct acgcggatgt cgccgatgtc agcgcggcgg atgacgacac cgtcaccgtg  1560
cgtgtgggtg acgccgagta tacgatcggc cgcaacggtg tgaccggcgg cgagggtgtg  1620
caggccaacg tcgtttcgtc tgatgccgga tacgaagtcg tggccgatat cccatacacc  1680
ggtgcagaga aggacatcgt cgagatgaac gtcatcgcga cggattccgc caccacggag  1740
accagcgcgt ggagcacgaa cgacaccggc gccgtcacgc tggccgagcc gctgagctac  1800
acggaagccg tgaaggttcc cgccgacgcc aagctccggg tcgttgacgc cgacccgtcg  1860
gatcccgtct gggcggaagc caacgaggtt cccgtggata aggtgaccgc cgccacgcct  1920
tcccccgagg cgaccgctac cgccaagacc ctgtggtcgg acggcaagct gtatgtcctc  1980
atggaagtga ccgacgcgga catcgacctg accaactcga atccgtggga aaggactcc   2040 gtggaggtat acatcgaccg cggcaacacc aagagcggcc agtacaccaa cgacatccag  2100
cagattcgcg tgtccgccga tgcgcgcgag ctgagcttcg gctccggcgc gtcggaggat  2160
gtccagaagt ccatggtcca gaccgccggc acgatcgtcg atggcggcta tgtcgtcgag  2220
atggccatcg atctgggaac ggctgaggcc ggcaccttcg aaggtgtcga cttccagatc  2280
aacgacgcga agaacggtgc ccgaatcggc atccgcaact gggccgatcc gaccggcgcc  2340
ggctatcaga cggcgtccca ttggggcgtg ctgcgtctgc tggccgattc ctccgaaacc  2400
```

| | |
|---|---|
| gagaccccg gcggcgagga gacccctggg gggggtaccg acaagcctgg cgacgagaag | 2460 |
| ccgcagcctt ccgacgatgc tgacaacgac gacaagatgc cgcagaccgg ttccgcggtc | 2520 |
| atcggagtcg ccgtggtggc gttgctgctg gttgccgccg gatgcgggct ggtcatcgct | 2580 |
| cggcgtcgat ga | 2592 |

```
<210> SEQ ID NO 2
<211> LENGTH: 2100
<212> TYPE: DNA
<213> ORGANISM: Bifidobacterium pseudocatenulatum

<400> SEQUENCE: 2
```

| | |
|---|---|
| gtggcagacc ttgatgcgga ttcgctgaac gaatcagctg aaaacacgca ggaagatcag | 60 |
| atccagaacg atcagctcga agatgcgcag ctcgatgaca ccttggctcc ggagcattac | 120 |
| gacgcttccg atctgagggt tctggaaggc cttgaggcgg tgcgaatccg cccgggcatg | 180 |
| tacatcggct ccaccggccc ccgaggcttg caccacctgg tgtacgagat cgtcgacaac | 240 |
| tccgtcgatg aggcgctggc aggctacgct tcgcacatcg aagtgacgat tctgccggac | 300 |
| ggcggcgtgc gcgtggtgga tgacggccga ggcattccgg tcgacgaagt gccgggcgaa | 360 |
| ggcgtttccg gcgtggaaac cgtgatgacc aagctgcatg ccggcggcaa gttcggtggc | 420 |
| ggcggctatg cggtttccgg cggtctgcac ggcgtgggca tctccgtggt gaacgcgctg | 480 |
| tcgacccgcg tcgacatcga agtgcgccga cagggcctcc actggaccca gacctacatc | 540 |
| gaccagaagc cgaccgcacg tcttgccaag ggcgagccga tgggcgaaga cgagtccacc | 600 |
| ggcacttccg tgaccttctg ggcagacggc gcgatcttcg aaaccaccac ctacgatttc | 660 |
| gagaccctgc gcaaccgctt ccagcagatg gcgttcctca caaggggct gaaactgtcc | 720 |
| ctgaccgatt tgcgcgaacc ggatcaggcc ggagacgaag tcgcgggcga aagcgacgac | 780 |
| aatgccgaac cgaagcatca gacggtcacc taccaataca cgacggcat caaggattat | 840 |
| gtcgattact tggtgaagtc ccgcaaggca accccgtcg aaccggacgt gatcgatttc | 900 |
| gaagcggaag acctgaaaat cggcattttcc gcggaaatcg ccatgcaatg gaccaccgca | 960 |
| tactccgaag cggtgcacac cttcgccaac accatctcca ccaccgaagg cggtacccac | 1020 |
| gaagaaggct tccgcgccgc gctgacctcg ctcgtcaacc gttacgcacg tgaaaagaac | 1080 |
| atcctcaaag acaaggatga gaacctctcc ggcgacgacg tgcgcgaagg cctgaccgca | 1140 |
| gtggtgtcgg tgaaactcac caccccgcag ttcgaaggcc agaccaagac caagctcggc | 1200 |
| aattccgaag cgaaaacctt cgtacagcgt gtgatgaccg acaagctcgg cgactggttc | 1260 |
| gattcgcatc ctagcgaggc caagaacatc atccagaagg ccattgaagc ctcccgtgcg | 1320 |
| cgtcttgcag ccaagaaggc acgtgagaat accgccgta agtcaatctt cgaatctgcg | 1380 |
| ggcatgccag acaaactgaa ggattgccag tccaacaatc ctgaagaatg cgaactgttc | 1440 |
| atcgtggagg cgactccgc aggcggctcc gcaattcagg acgcaaccc gatcacgcag | 1500 |
| gccatcctgc cgttgcgagg caaaatcctt aacaccgagc gtgcaagcct cgaccgcatg | 1560 |
| atgaagtccg aaaccatcga atcgctgatc accgcggtcg cgcgcggcta tggcgaggat | 1620 |
| ttcgacctga caaagtccg ctaccacaag gtcatcatca tggccgatgc cgatgtggac | 1680 |
| ggcgcgcata tcgcaaccct gaatctgacg ctgttcttcc gctacatgcg cccgatgatc | 1740 |
| accgctggtt acgtgtatgt ggccatgccg ccgctgtacc gactcaagtg gaccaaaggc | 1800 |
| gcgcacgact tcgtgtacac cgacgccgaa cgcgaccgcg tgctcgccga aggcaagtcc | 1860 |

| | |
|---|---:|
| gccggccgtc agctgccgaa gggcgaaggc atccagcgtt acaagggtct gggtgaaatg | 1920 |
| agctaccagg aactgtggga aaccaccatg gatcctgacc accgcattct gaagcaggtg | 1980 |
| cagatcgaag acgcggccgc agccgacgaa accttctcca tgctcatggg agacgaagtc | 2040 |
| gaacctcgcc gtctgttcat ccagcgcaac gcccgcaacg tcagctggat cgacgcgtag | 2100 |

```
<210> SEQ ID NO 3
<211> LENGTH: 831
<212> TYPE: DNA
<213> ORGANISM: Bifidobacterium pseudocatenulatum

<400> SEQUENCE: 3
```

| | |
|---|---:|
| atggctatcc gcgtttataa gccgacgact gcaggccgcc gtaacgcgtc cgtctcggac | 60 |
| ttctccgagc ttacgcgttc tacgcctgag aagtcgctgg ttcgcaaact cagcaagact | 120 |
| ggcggtcgta actcttacgg ccgtatgacc tcccgtcatc gtggcggcgg tcacaagcgc | 180 |
| cagtaccgtc tcatcgactt caagcgttgg gacaaggacg gcgtgccggc aacggtcgct | 240 |
| cacatcgagt acgacccgaa ccgttccgcc cgcatcgcac tgctgcacta cgcagacggt | 300 |
| gagaagcgct acatcatcgc tccggaaggt atcaagcagg gtgacgtcat cgagaccggc | 360 |
| gcccaggctg atatcaagcc gggcaacaac ctgccgctgc gcaacatccc gactggtacc | 420 |
| gtggtgcacg caatcgagct ccgcccgctg ggtggcgcca agatcgcccg ctccgctggt | 480 |
| gcagccgtgc agctcgtcgc taaggatggc gcttacgccc agctgcgtat gccgtccgga | 540 |
| gaaatccgca acgtggatgc tcgctgccgc gcaaccgtcg gtgaggtcgg caactccgat | 600 |
| cacgccaaca tccagctcgg taaggcaggt cgtgcacgtt ggatgggcaa gcgcccgatc | 660 |
| acccgtggtg aatccatgaa ccctgtcgat caccgcacg gcggtcgtac ccgcggtggc | 720 |
| aagccgccgc tttctccgtg gggcaagggc gaggttcgta cccgccgtcc gaagaaggct | 780 |
| tcgaacaaga tgattgttcg tcgtcgcccg aatggtaaga accgtaagta a | 831 |

```
<210> SEQ ID NO 4
<211> LENGTH: 1515
<212> TYPE: DNA
<213> ORGANISM: Bifidobacterium pseudocatenulatum

<400> SEQUENCE: 4
```

| | |
|---|---:|
| ttgtcagctg aactcgaaga catccacgag gaatgcggta tttttggcgt ttggggtcac | 60 |
| ccggacgccg cccgactcac ctacttcggc ctgcacgcgc tgcagcatcg tggtcaggaa | 120 |
| ggcgccggca ttgtctcgaa cgataacggt catctcatcg gtcatcgcgg aacgggtctg | 180 |
| ttgacccaag tgttcggcga cgaacgcgaa atcgaacgcc tgaagggaga caaggcgatc | 240 |
| ggccatgtgc gttacgccac tgccggttca ggcggcaccg acaacatcca gccattcatc | 300 |
| ttccgcttcc atgacggcga tatggccttg tgtcacaatg gcaatctgac gaactgcccg | 360 |
| actctgaggc gtcagttgga agacgaaggc gcaatcttcc actccaattc cgacaccgaa | 420 |
| gtgttgatgc acctgttgcg ccgctccaca cagcgtacgt tcatggacaa gctcaaggaa | 480 |
| gcgctcaaca ccgtgcatgg cggtttcgcc tacctgatca tgaccgaaga cgccatgatc | 540 |
| ggcgcgcttg atccgaacgg tttccgcccg ctttccctcg gcaagatgaa aaacggcgct | 600 |
| tatgtgctcg cttccgaaac ctgcgcgctt gacgttgtcg gcgccgaatt ggtgcgcaat | 660 |
| attcgcccgg gcgaaatcgt ggttatcgac gatcacggct acaagatcgt gcagtacacc | 720 |
| aatcagaccc agttggccat ctgctcgatg gaattcatct acttcgcacg ccccgattcc | 780 |
| gacatttacg gcgtaaacgt gcattccgcc cgcaagcgta tgggtgcgcg tctggcccaa | 840 |

-continued

```
gaatcgccgg tcgatgccga tatggtcatt ggcgtgccga attcctcgct gtccgcggcc      900
tccggctatg cggaagaagc tggtctgcca acgagatggg cctgatcaa gaaccagtat      960 gtggctcgaa ccttcatcca gccgacgcag gaactgcgcg agcagggcgt gcgcatgaag     1020
ctgtccgccg tgcgcggcgt ggtcaaaggc aagcgcgtga tcgttatcga cgattccatc     1080
gtgcgcggta ccacgtccaa gcgcatcgtg cagctgctga aggaagctgg cgccgccgaa     1140
gtgcacatgc gtatcagctc gccgccgctg aagtacccgt gcttctacgg catcgacatc     1200
tccaccacca aggagctcat cgccgcaaag aagtccgttg aagaaattcg cgatttcatt     1260
ggcgccgatt ccttggcgtt cctgtcactc gacggattgg tcgaatctat cggcctgggt     1320
gcggacgccc cgtacggcgg tctgtgcgtg gcctacttca atggcgacta cccgaccgca     1380
ctcgacgatt atgaaagtga ttttttgaag tccctcaccc cagaagatcg cgtgcgtctg     1440
cctgaattcg ccttgtataa gagcaagtac gagggcaacg aatacaccac tacttcatcc     1500
caagaagaac actga                                                      1515
```

<210> SEQ ID NO 5
<211> LENGTH: 3561
<212> TYPE: DNA
<213> ORGANISM: Bifidobacterium pseudocatenulatum

<400> SEQUENCE: 5

```
ttggctgagg ctacgacgaa caccaccacc atcatcgcac gcgccgacca gcacgatatt       60
gatctgcaca aggcgtcgga ccgtgtgaac ttcggctcca tccgcgagcc cattgatgta      120
ccctacctgt tgggtgtaca gactgacagc ttcgactggc tcatcggcaa cgagcgctgg      180
cagaagcgtg tcgaggagga tctggcgaac ggcaccaaca ccgtgcccca cacctccggt      240
cttgatgagg tcttccagga gatctcaccg atcgagaact tcgctcagac catgagcctg      300
accttctccg atccgtattt cgaagaaccg cgccacaccg tgcaggagtg caaggagaag      360
gattacacct actccgcgcc gctgtatgtg aacgctgaat cgaaaacggc gacaccggc      420 gaaatcaagt cccagaccgt gttcatgggc gatttcccgc tgcagacccc gcacggcacc      480
ttcatcatcg gtggtaccga gcgagtgatc gtgtctcagc tggtgcgttc tccgggcgtg      540
tacttcgacc gcagccagga tcgcacttcc gacaaggaag tcttcggcgc gaagatcatc      600
ccgagccgtg gcgcatggct tgagttcgag atcgacaagc gtgacgtgct ggcgtgcgc      660 gtggaccgca agcgcaagca gtccgccatc gtgttcctca tggccatcgg catgaccaag      720
gatgagatcg ccgatgcgtt cagggattac ccgctggtta tggacgcgct tgccaaggag      780
accgtgcaga cccaggacga ggctctgacc gatctgtacc gcaagatccg cccggccgac      840 acccgacgc cggaagctgg ccgcaacctg ctggattcct tctacttcaa caccaagcgt      900
tacgatctgg cccgcgttgg ccgttacaag atcaaccgca agcttggtct ggaaaaggat      960
gtcaacgatc gcagcctgtc tcgcgaagac atcatctcca ccatcaagta cctggtcacc     1020
ctgcatgccg gcgacaccaa gttcccgggc aagcgtgacg gccaggatgt ggatctgcgc     1080
gtggacgtcg acgatatcga tcatttcggc aacgtcgta tccgccaggt cggcgaactg     1140
atccagaacc agctgcgtac cggtctgagc cgtatggagc gtgtggtccg gaacgtatg      1200 accacccagg atccggaggc catcacccg cagtccctga tcaacattcg tccggtgaac     1260
gccaccatca aggagttctt cggaacttcc cagctgtcgc agttcatgga tcagaacaac     1320
ccgttggcag gcgtcaccaa caagcgtcgt ctgtccgctc tgggcctgg cggtctgtct     1380
```

-continued

```
cgtgaccgcg catccatgga agtgcgagac gtgcacccgt cccacttcgg ccgtatgtgc    1440
ccgatcgaat ctcctgaagg tccgaacatc ggtcttatcg gttctctggc aaccttcggc    1500
cgcatcaatc cgttcggctt catcgagacc ccgtaccgta aggtcatcaa cggccatgtg    1560
accgacgagg tcgaatacat gaccgcgac cgcgatgccg agcacgtgat cgcacaggcc     1620
aaccaggaac tcgacgagaa cggcaacttc gtcaagaagc aggctcttgc ccgagtcggc    1680
gaagaagaag cagtcgatgt gcccgtcagc tccgttgact acatggacgt ttccccgcgt    1740
cagatggttt ccgtcggcgc ctccctgatt ccgttcctgg agcacgatga gggccaccga    1800
gcgctgatgg gtaccaacat gcagcgtcag gcagtgccgc tgatcgaatc cgagcgcccg    1860
ctggtgggca ccggtgccga atggcgtgcg gccgtcgatt ccggcgatgt cattctggct    1920
gagaagccgg gtgtggtgac gtatgttccc gccgacatca tccgtgtgat gaacgacgac    1980
ggcaccacca gctcctacaa gctggccaag ttcctgcgtt ccaaccagac cacctgctac    2040
aaccaggttc cgctgatcca cgacggcgaa cgtgtggaag ccggtaccgt gcttgccgat    2100
ggtccggcca cccagaaggg cgaaatggca ctgggcaaga acctgctcat cgccttcatg    2160
ccgtggaacg gctacaacta cgaggatgct gtgatcatct cccagcgtct cgtgcaggac    2220
gacaccctga gctccatcca catcgaggaa tatgagatca cgcccgcga aaccaagctg      2280 ggtgccgaag agatcacccg cgatctgccg aacgtcggcg aggacgcggt ggccaacctc    2340
gacgagcgtg gcatcattcg catcggtgcc gaggtcgaag ccggcgacat tctggtgggc    2400
aaggtcaccc cgaagggcga gaccgagctg actccggaag agcgtctgct ccgcgccatc    2460
ttcggcgaga gagccgcga ggtgcgtgac acctcgctgc gcgtgcctca cggcgaaacc       2520
ggtacggtga tcgccgtcaa ggagatcact cgcgaggatg ccgaggaaga cggcgacgag    2580
ctgccgaacg gcgtgaacca gatgatccgc gtctacatcg cgcagcatcg taagatcacc    2640
cagggagaca agctgtccgg ccgccacggc aacaaggtg ttatctcccg cattctgccg      2700
gaagaggata tgccgttcct tgccgacggt actccggtcg acatcatgct gaacccgctg     2760
ggcgtgcctt ctcgaatgaa ccttggccag gtgctggaac tgcacttggg ctggatcgcg    2820
cacgccggct gggacatctc ccttgatccg gatgccgaag ccgcttggaa gaagtacatt    2880
ccgcagggcg ccgaaaaggg cgagccgggc actccggtgg caaccccggt gttcgacggc    2940
gttcgtccgg aaaccatcaa gggcctgctg tcctgcaccc ttccggatcg cgacggcaac    3000
aagctggtcg gcgacgacgg caaggctgtg ctgttcgacg gccgtaccgg cgaaccgtat    3060
ccgaagccga tctccgttgg ctacatgtac atgctgaagc tgcaccacct agtcgacgac    3120
aagatccacg cgcgttccac tggcccgtac tccatgatca cccagcagcc gttgggcggt    3180
aaggctcagt tcggtggcca gcgtttcggc gagatggaag tgtgggccct cgaggcctat    3240
ggcgccgcct acacgctgca tgaaatgatg accaccaagt ccgatgacgt cgacggccgc    3300
gtgcgtgtct acgcgccat cgtgaagggc gacaacctgc cgccggcagg cattccggaa      3360
tccttcaagg tgctgcttaa ggaaatgcag tccctgtcgc tgaacgtcga agtgctcaac    3420
gccgaaggcg tggccatcga catgaaggac gaggacgacg atccgtctac ttcctccgac    3480
gatttgggct tcaacattgg cgcacgtcct gacgcggccg ccaaggaaga ccaggttgtg    3540
gaagaacctg aattccagtg a                                              3561
```

<210> SEQ ID NO 6
<211> LENGTH: 2586
<212> TYPE: DNA
<213> ORGANISM: Bifidobacterium pseudocatenulatum

<400> SEQUENCE: 6

```
atgttcgaac ggtttaccga ccgtgcgcgg cgcgtgatcg tgctggcgca ggaagaggct    60
cgtaccctcc agcacaacta catcggtacc gagcatctgc tgcttggcct gattcgtgag   120
ggtgacggcg tcgcagccaa ggcgctggcc tcaaagggtg tgaccttgga tgacacccgc   180
aaacaggtcg aagagatgat cggtaagggg aatgccacgc gaacggcca cattcccttc    240
accccgcatg ccaggcaggt gttggagctg tcgctgcgtg aggcgttgca gctggggcac   300
agctatatcg gcaccgagca tatcctgctc ggtctgattc atgaaggcga aggcgtcggc   360
acccaggtcg tgatcaagat ggacgtcaat cttggcgagc tgcgcagcgc caccatcgac   420
ctgatccgtg gcaattccgg tgatggcaag ggcgatggca agggcgattt ggccaatgcc   480
ggtggcgtgc aggatcgtcg caaccagacc ggttccgcga ttcttgacca gttcggccgc   540
aatctgaccg ctgaagctgc cgccggcaag cttgatccgg tgattgggcg ttcgagtgag   600
atcgagcgtg tgatggtggt gctgagccgc cgtaccaaga caatccggt gctgatcggc    660
gagccgggtg tcggcaagac ggccgtggtc gaaggcttgg cgcagaagat caatgccggc   720
gacgttccgg agacgctgaa gggcaagcag gtctattcgt tggatctggg atccatggtg   780
gctggttcgc ggtatcgtgg cgatttcgag gagcgtctga agaaggtgct caaggagatc   840
aagacccgcg cgacatcgt gctgttcatc gatgagatcc ataccattgt gggcgctggt    900
tccgcggatg cgctcttgg cgcttccgac atgttgaagc caatgctcgc gcgaggtgag    960
ctgcagacca ttggcgccac caccaccgac gagtaccgta agtacatcga aggatgcc    1020
gctttggaac gtcgtttcca gcccatccag gtgcatgagc cgagcattgc cgaaaccatc   1080
gagatcctta agggcttgcg ttcgcgttac gagaaccatc accatgtgac gatcaccgat   1140
ggtgcgttgc aggccgcggc cgatctgtcg agccgttaca ttcaggaccg tcatctgcca   1200
gacaaggcca tcgatctgat cgatgaggcc ggtgcgcgtc tgcgcatccg tcgtctgacc   1260
gctccgccgg agcttaagga acttgacacg aagatcgcca agcttgccga agagaaggac   1320
caggccatca agggccagga cttcgaaaag gccgctgagc tgcgtgataa gcaggagaag   1380
ctggaagccg aacgcaagca gaaggaatct tcgtggcgtg agggcgaatc cgatgtgaag   1440
atggttgtgg atgaggatgt catcgccgaa gtgatttccc agaccaccgg cattccggtg   1500
ttcaagctca cccaggccga gtccaagaag ctcatgacca tggaaagcga gctgcacaag   1560
cgcatcatcg ccaggacga ggccgtgtcc gcgttgagcc gctccatccg tcgtgctcgt    1620
gttggtttga aggatccgaa gcgtccgtcc ggttcgttta tcttcgctgg ccccaccggc   1680
gtcggtaaga ccgagctggc caagacgctc gccgaattcc tgtttgacga cgaggacgca   1740
ctgattcgtg tcgacatgtc tgaattctcc gagaaatatg cggcttcgcg cctatttggt   1800
gctcctccgg gatacgtcgg ttacgaagag ggcggcgaac tcaccgagaa ggttcgtcgc   1860
aagccgttct ccgtggtgct gttcgatgag atcgaaaagg cccatccgga tatcttcaac   1920
acgctgctgc aggtgcttga tgacggtcat ctgactgatg gccagggccg caaggtggac   1980
ttcaagaaca ccatcatcat tctgaccacc aatcttggta cgcgagacat cgccaaggcc   2040
gccaacaccg gcttcaactt gggtgccaac accgagtcga gctaccagcg catgaaggat   2100
caggtttccg cggagctgaa gcagcagttc cgtccggaat tcctgaaccg tctggacgac   2160
atcatcgtgt tcaagcagct caccgagccg aagtgcgtc agatcgtcga tcttgacgtc   2220
aagcagctca atgatcgctt gttcgatcgc cacatgtccc tcgagcttac cgacgctgcc   2280
```

```
aaggatctgc tcgcgcagaa gggcttcgac ccgctgctgg gcgcgcgtcc gttgcgtcgc    2340
gtgattcagc gcgacgtcga agacgccatt tcggagaaga tcctgatggg cgaactcgaa    2400
gatggccagc gcgtgaaggt cgatgcggaa ggcgaaggca tcctgggcga gttcaccttt    2460
accggtgagg cgttcgaaga gccaaatacg gagcctgctg aaggtgaagt cgcagctgaa    2520
accgaggcac ctgccgaatc gacggaatcg acagaactta cggaatccgc agaatctgtt    2580
gaataa                                                               2586

<210> SEQ ID NO 7
<211> LENGTH: 2130
<212> TYPE: DNA
<213> ORGANISM: Bifidobacterium pseudocatenulatum

<400> SEQUENCE: 7
atggcactag acgtgctcaa tgatctcaac cagatccgta acatcggcat catggctcac      60
atcgatgccg gtaagaccac taccaccgaa cgtatcctgt actacaccgg caagaactac     120
aagatcggcg agacccatga cggtgcctcg acgatggact tcatggctca ggagcaggaa     180
cgcggcatca ccatccagtc cgctgcaacc acttgcttct ggaaccgtca gacccatgac     240
gagaagcaga agttccagat caacatcatc gataccccag ccacgtggac cttcacggcc     300
gaggtggagc gctccctgcg cgtgctcgat ggtgccgttg ccgtgttcga cggcaaggaa     360
ggtgtggagc gcagtccgga gaccgtgtgg cgtcaggctg acaagtacgg cgttccgcgt     420
atctgcttca tcaacaagat ggataagctc ggcgctgact tctactactc cgtcgacacc     480
atcaaaacca agctgggcgc gaccccgctt gtcgtgcagc tgccgatcgg cgctgagaac     540
gacttcgctg gcgttgtcga tctgattcgt atgaaggctt acgtctggaa cgacgtttcc     600
ggcgacatgg gcgctcacta cgacactacc gacatccccg ccgacctgca ggacaaggcc     660
gagcagtatc gtgcagagct gctcgaccag gtcgcagaat ccgacgaaga gctgcttgag     720
aagtatctcg agtccggcga actgactgag gacgagatcc gtagcggcat ccgtaagctc     780
accattaacc gtgaagccta cccggtgctc tgcggctccg ccttcaagga caagggtgtt     840
cagccgatgc tggacgccgt cgtcgactac ctgccgagcc cggaggacgt tccgtccatc     900
gtcggtttcg atcctaagga cgaatccatc gagatcgatc gcaagccgac caccgatgat     960
ccgttctctg ccctggtctt caagatctct cccaccccgt tctacggcaa gctcgtgttc    1020
gtgcgcgtct actccggcgc cgtcaccccg ggcgacaccg tgcttgactc caccaagggc    1080
aagaaggaac gcgtcggcaa gatcttccag atgcacgccg acaaggagaa cccggtcgat    1140
gccgccgaag ccggcaacat ctacaccttc gtgggcctga gaacatcac caccggtgac    1200 accctgtgcg acgaaaaggc gcctatctcc ctcgaatcca tgaccttccc ggatccggtg    1260
atcgaggtgg ccgtggagcc gaagaccaag gccgatcagg agaagatgag catcgctctg    1320
gcgaagctgt ccgacgaaga tccgaccttc caggtgaaga ccgacgaaga gtccggccag    1380
accctgatct ccggcatggg cgagctgcag ctcgacatca tcgtcgaccg tatgcgtcgt    1440
gaattcaagg tggagtgcaa cgtgggtaac ccgcaggttg cataccgtga cgatccgcc     1500 aaggccgtca tgaaccagga atacacgcac aagaagcaga ccggtggttc cggccagttc    1560
gcaaaggtct tgatgaactt cgagccgctc aacaccgaag agggcgagac ctacgagttc    1620
gtcaacgagg tcaccggtgg ccacatcacc aaggaattca ttccttccat cgatgctggt    1680
gtgcaggaag ccatggaatc cggcgtgctc gccggcttcc cggtggttgg cgtcaaggct    1740
accgtcactg acggccaggt ccacgacgtc gattcctccg aaatggcctt caagatcgca    1800
```

```
ggttccatgt gcttcaagga agctgctccg aaggccaagc cggtcatcct cgagccgatc      1860
atggccgtgg aagtgcgtac tccgaagag tacatgggcg acgtgatggg cgatatcaac       1920
gcccgtcgtg gttccatcca gtccatgacc gactccaccg gtgtcaaggt catcgatgcc      1980
aaggttccgc tgtccgaaat gttcggctac atcggcgacc ttcgctccaa gacccagggc      2040
cgcgcaatgt tcaccatgca gatggactcc tacgctgagg ttccgaagaa cgtctccgag      2100
gagatcatca aggcccagcg cggcgagtga                                       2130

<210> SEQ ID NO 8
<211> LENGTH: 3312
<212> TYPE: DNA
<213> ORGANISM: Bifidobacterium pseudocatenulatum

<400> SEQUENCE: 8
gtgagcgaaa acaacgtgta tccgaaggca gctgcgggtg agcagagcgc caatgtagcg        60
ccgaacccca gtttcccgaa gctggaagaa tccgtccttg attattggga gaaggacgac       120
actttccaga agtccattga acgccgtcct tccggcgatc acagccagaa cgaattcgtc       180
ttcttcgacg gaccgccgtt cgccaacggc ctgccgcact acggccacct gctgaccggc       240
tacgccaagg atgtgattcc gcgctaccag accatgaagg gccacaaggt caatcgtgtg       300
ttcggctggg atacgcacgg tctgccggcc gagcttgaag cccagaagga actgggcatc       360
gactcggtcg atcaggtcaa ggaaatgggc atcgacaagt caacgacgc ttgccgcgcc        420 tccgtgctca gtacaccaa cgagtggaag gactacgtgc accgtcaggc acgttgggtc        480
gatttcgagc atggctacaa gacgctgaac attccataca tggaatccgt gatgtgggcg       540
ttcaagcagc tgtacgacaa gggcctcgca tatcagggct accgcgtgct gccgtactgt       600
ccgaaggatc agacgccgct ttccgcgcac gagctgcgca tggacgccga cgtgtatcag       660
gatcgtcagg acaccaccgt gtccgtggcc gtgaagctgc gcgacgagga agacgcctat       720
gcggtgttct ggaccaccac gccgtggacc gttcccacca cttcgccat cgtggtcggc        780 gcagacatcg actatgtgga agtgcgtccg accgaaggca agttcgcggg caagaagttc       840
tacctgggca agccactgct cggctcctac gccaaggaac ttggcgacaa ctatgagatc       900
gtgcgcgaac tcaagggtgc cgagatggaa ggctggcgct actaccggt gttcccgtac        960 ttcgcaggc acgagaacgc cgtcgaaggc aaggttccgg tccggaagg ctatcagatc       1020 ttcaccgccg actatgtcga taccgttgag ggtaccggtc tcgtgcacca ggctccgtac      1080
ggcgaggacg atatgaacac gctcaacgcc aagggcatca gagcgttga cgtgctcgac       1140 gcgggctgca agttcaccgc gctgtgcccg gactacgagg gcatgtacgt gttcgatgcg      1200
aacaagccga ttctgcgtaa cctgcgtgcc ggtgacggtc tctggagcg tattccggaa      1260 gatcagcgcg cgatccttt ccaggagaag agctacgtgc actcctaccc gcactgctgg       1320
cgttgcgcca cgccgctcat ctacaagccg gtgagctcgt ggttcgtgtc cgtcaccaag      1380
atcaaggatc gtctgctcga actgaaccag gaaatcaact ggattccggg caatgtgaag      1440
gacggccagt cggcaagtg gctggccaac gcccgtgact ggtcgatctc ccgcaaccgt       1500
ttctggggtt cgccgattcc ggtgtggggtt tccgatgatc cgaagtatcc acgcgttgac      1560
gtgtacggtt cgttggacga gctgaaggct gattttggcg attatccgcg cgaccatgag      1620
ggcaatgtca acatgcaccg cccgtacatc gacgagctga cccgcgtcaa cccgacgat       1680 ccgaccggca agagccacat gcaccgcatc accgacgtga tggactgctg gttcgaatcc     1740
```

```
ggttccatga gcttcgccca gtaccattac ccgttcgaaa acaaggaaac gttcgaacag    1800
catttcccgt gcgattacat cgtggaatac atcggccaga cccgtggctg gttctacgtg    1860
cagcacatca tggcgaccgc actgttcgac aagccggcgt tcaagaacgt gatctgccat    1920
ggcatcgtgc ttggctccga cggccagaag atgtcgaagc atctgcgcaa ctacccggat    1980
gtgaatggag tgttcaacga tttcggctcc gacgccatgc gctggttcct catgagctcg    2040
ccgatcctgc gcggcggcaa cctgatcgtg accgccgatg gcattcgcga caccgtgcgt    2100
caggtcatgc tgccagtgtg gagttcgtac tacttcttca ccctgtatgc gaacgccgcc    2160
aataatggcg ccggcttcga tgctcgtaca ttgcgtgccg atgaggtcgc cgcactgccg    2220
gaaatggatc gttacctgct ggcgcgtacc cgccgactga tcgagaagac gcaaagctcg    2280
ctggacaact tcctgatctc tgacgcatgc gaagccgtgt ccgatttcat tgacatgctc    2340
accaactggt atatccgcaa caatcgtgac cgtttctgga atgaggatgc gaacgcgttc    2400
aacacgctgt acaccgtgct tgaagcattc atgcgcgtga tcgcaccgct tgctccgatg    2460
gaagcggaag cagtgtggcg tggtctgacc ggtggcgaat ccgtgcactt ggccgactgg    2520
ccgttccttg ccgacgagca gaccggagag gcaacagaac tgggccgcgt gcttgttgac    2580
gatccggctc tggttgatgc gatggagaag gtgcgcgagg tcgtgtccgg cactctgtct    2640
atgcgtaaga caaagcagat ccgtgtgcgc cagccgctgt ccaagctgac cgtggtggtg    2700
gagaacactg ccgccgtggc cgcatacgac gagattctga atccgaact gaacgtgaag    2760 aacgttgaat tgtgcacgct tgaagatgcc gaagcccaag gcttgaagat catcaacgag    2820
ctgcgtgtga acgctcgcgt ggcaggcaag cgcctgcgca aggacgtgca gttcgccatc    2880
aaggcttcca gtccggcgc atggcatgtg aacgccaag gcgctccggt atgtgagact    2940
ccgaacggtg agatcgtgct tgaggaaggc gaatatgagc tgatcaacag cgtggaggag    3000
aagaacgccg aagaggccgc caactctgta agtgctgcac tgccgaccgg tggcttcgtg    3060
atcctcgaca ccgagctgaa cgacgatctg atcgcagaag gctatgcccg cgacgtgatc    3120
cgcgccgtgc aggacgcccg caaggccgcc gatctgcaga tctccgaccg tatcgcactg    3180
aagctcgttg tgcccgccga agacgtggcc aaggtcgaac agttcaagga acttgtctcc    3240
tccgagacgc tcgccacttc cttcgaagtg actgccggcg atgagctgaa cgttgaggtt    3300
gccaaggcct ga                                                        3312
```